(12) United States Patent
Lam

(10) Patent No.: US 10,492,938 B2
(45) Date of Patent: Dec. 3, 2019

(54) SYSTEM AND METHOD FOR IMPLANT DELIVERY

(71) Applicant: Terumo Corporation, Tokyo (JP)

(72) Inventor: Cang Lam, Tustin, CA (US)

(73) Assignee: Terumo Corporation, Tokyo (JP)

( * ) Notice: Subject to any disclaimer, the term of this patent is extended or adjusted under 35 U.S.C. 154(b) by 388 days.

(21) Appl. No.: 15/234,906

(22) Filed: Aug. 11, 2016

(65) Prior Publication Data

US 2017/0042548 A1 Feb. 16, 2017

Related U.S. Application Data

(60) Provisional application No. 62/203,882, filed on Aug. 11, 2015.

(51) Int. Cl.

| A61F 2/97 | (2013.01) |
|---|---|
| A61F 2/01 | (2006.01) |
| A61F 2/95 | (2013.01) |
| A61F 2/966 | (2013.01) |
| A61B 17/12 | (2006.01) |
| A61B 17/00 | (2006.01) |
| A61B 17/22 | (2006.01) |
| A61B 90/00 | (2016.01) |

(52) U.S. Cl.
CPC .............. *A61F 2/97* (2013.01); *A61F 2/01* (2013.01); *A61B 17/1204* (2013.01); *A61B 2017/00336* (2013.01); *A61B 2017/1205* (2013.01); *A61B 2017/22042* (2013.01); *A61B 2090/037* (2016.02); *A61F 2/013* (2013.01); *A61F 2002/011* (2013.01); *A61F 2002/9505* (2013.01); *A61F 2002/9665* (2013.01)

(58) Field of Classification Search
CPC ......... A61B 17/1204; A61B 2017/1205; A61F 2002/011; A61F 2/01; A61F 2/013; A61F 2/97

See application file for complete search history.

(56) References Cited

U.S. PATENT DOCUMENTS

| 4,166,469 | A |   | 9/1979 | Littleford |
| 4,631,059 | A |   | 12/1986 | Wolvek et al. |
| 4,687,469 | A |   | 8/1987 | Osypka |
| 4,997,424 | A |   | 3/1991 | Little |
| 5,188,606 | A |   | 2/1993 | Maloney et al. |
| 5,261,887 | A |   | 11/1993 | Walker |
| 5,290,241 | A | * | 3/1994 | Kraus ............... A61M 25/0169 604/158 |

(Continued)

FOREIGN PATENT DOCUMENTS

WO WO2001/085991 A2 11/2011

OTHER PUBLICATIONS

WIPO, U.S. International Search Authority, International Search Report and Written Opinion dated Oct. 24, 2016 in International Patent Application No. PCT/US2016/046620, 17 pages.

(Continued)

*Primary Examiner* — Alexander J Orkin

(74) *Attorney, Agent, or Firm* — Inskeep IP Group, Inc.

(57) ABSTRACT

An implant delivery system is described. The implant delivery system utilizes an implant, implant wire, delivery sheath, and a torque device. The torque device may include a cutting element to slit the delivery sheath and a clamp device to fix the position of the implant delivery wire.

10 Claims, 5 Drawing Sheets

(56) References Cited

U.S. PATENT DOCUMENTS

| | | | |
|---|---|---|---|
| 5,324,269 A | 6/1994 | Miraki | |
| 5,330,460 A | 7/1994 | Moss et al. | |
| 5,687,727 A | 11/1997 | Kraus et al. | |
| 5,873,858 A | 2/1999 | Schafer et al. | |
| 6,142,987 A * | 11/2000 | Tsugita | A61F 2/01 604/500 |
| 6,159,198 A | 12/2000 | Gardeski et al. | |
| 6,171,327 B1 * | 1/2001 | Daniel | A61F 2/01 606/159 |
| 6,248,092 B1 | 6/2001 | Miraki et al. | |
| 6,251,119 B1 | 6/2001 | Addis | |
| 6,280,433 B1 | 8/2001 | McIvor et al. | |
| 6,497,681 B1 | 12/2002 | Brenner | |
| 8,012,127 B2 * | 9/2011 | Lieberman | A61M 25/0668 604/160 |
| 8,287,584 B2 | 10/2012 | Salahieh et al. | |
| 2002/0123755 A1 | 9/2002 | Lowe et al. | |
| 2003/0158565 A1 | 8/2003 | Gardeski et al. | |
| 2003/0176889 A1 | 9/2003 | Boyle et al. | |
| 2005/0004595 A1 | 1/2005 | Boyle et al. | |
| 2005/0182435 A1 | 8/2005 | Andrews et al. | |
| 2006/0167417 A1 | 7/2006 | Kratz et al. | |
| 2007/0167930 A1 | 7/2007 | Eversull et al. | |
| 2007/0175049 A1 | 8/2007 | Goode et al. | |
| 2007/0185524 A1 | 8/2007 | Diaz et al. | |
| 2008/0091137 A1 | 4/2008 | Reavill | |
| 2008/0108972 A1 | 5/2008 | Andrews et al. | |
| 2008/0154207 A1 | 6/2008 | Hardin | |
| 2008/0319387 A1 | 12/2008 | Amisar et al. | |
| 2008/0319524 A1 | 12/2008 | Yachia et al. | |
| 2009/0049698 A1 | 2/2009 | Drake et al. | |
| 2009/0054840 A1 | 2/2009 | Drake et al. | |
| 2009/0071012 A1 | 3/2009 | Shan et al. | |
| 2009/0234443 A1 | 9/2009 | Ottma et al. | |
| 2009/0254169 A1 | 10/2009 | Spenser et al. | |
| 2010/0030154 A1 | 2/2010 | Duffy | |
| 2010/0030161 A1 | 2/2010 | Duffy | |
| 2011/0106097 A1 | 5/2011 | Mahlin | |
| 2011/0137395 A1 | 6/2011 | Fargahi | |
| 2012/0029421 A1 | 2/2012 | Drake et al. | |
| 2012/0029474 A1 | 2/2012 | Drake et al. | |
| 2012/0029482 A1 | 2/2012 | Drake et al. | |
| 2012/0215071 A1 | 8/2012 | Mahlin | |
| 2012/0215171 A1 | 8/2012 | Christiansen | |
| 2012/0227561 A1 | 9/2012 | Grauhan et al. | |
| 2013/0184805 A1 | 7/2013 | Sawada | |

OTHER PUBLICATIONS

WIPO, International Preliminary Examining Authority (U.S. Patent and Trademark Office), International Preliminary Report on Patentability dated Feb. 2, 2018 in International Patent Application No. PCT/US2016/046620, 8 pages.

* cited by examiner

SYSTEM AND METHOD FOR IMPLANT DELIVERY

RELATED APPLICATIONS

This application claims priority to U.S. Provisional Application Ser. No. 62/203,882 filed Aug. 11, 2015 entitled System and Method of Implant Delivery, which is hereby incorporated herein by reference in its entirety.

BACKGROUND OF THE INVENTION

Implants may need to be delivered to various regions of the vasculature for many reasons. For example, embolic coils may be delivered to target regions of the vasculature to occlude a space, stents may be delivered to a target region to divert flow away from an area or prop open a blood vessel, embolic protection devices ("EPDs") or blood filters may be delivered downstream of a target region to catch thrombus dislodged during a stenting or ballooning operation to prop open a blood vessel, clot retrievers may be delivered to a target region to capture and remove thrombus.

Implant delivery can be difficult due to the small size of many blood vessels, high turbidity due to blood flow, tortuous anatomy, as well as other reasons. A typical method for delivering an implant involves either pushing the implant out from a catheter/delivery device or retracting the catheter/delivery device to expose the implant. Generally, the implant is strategically placed so that upon deployment the implant will be at or near the target site. Because of the difficult conditions encountered in the vasculature, the implant may shift considerably when pushed from the delivery device or when the delivery device is retracted.

An implant delivery system and method that can quickly and accurately place an implant at a treatment site is therefore desirable.

SUMMARY OF THE INVENTION

An implant delivery system is described.

In one embodiment, the implant delivery system includes an implant, an implant wire that carries the implant, a sheath, and a torque device. The torque device includes a cutting element and accommodates a portion of the sheath and a clamping device for fixing the position of the implant wire. The sheath can be retracted through the torque device to cut the sheath and separate it from the implant wire.

In one embodiment, a separator tube is located adjacent to the cutting element within the torque device. The separator tube guides the sheath through a separate sheath lumen during the cutting operation.

In one embodiment, the cutting element is located along the sheath lumen in the torque device.

In one embodiment, the torque device includes a clamp element. The clamp element can be used to selectively compress a collet on to the implant wire.

In one embodiment, the implant delivery system is used to deliver an embolic protection device or a filter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
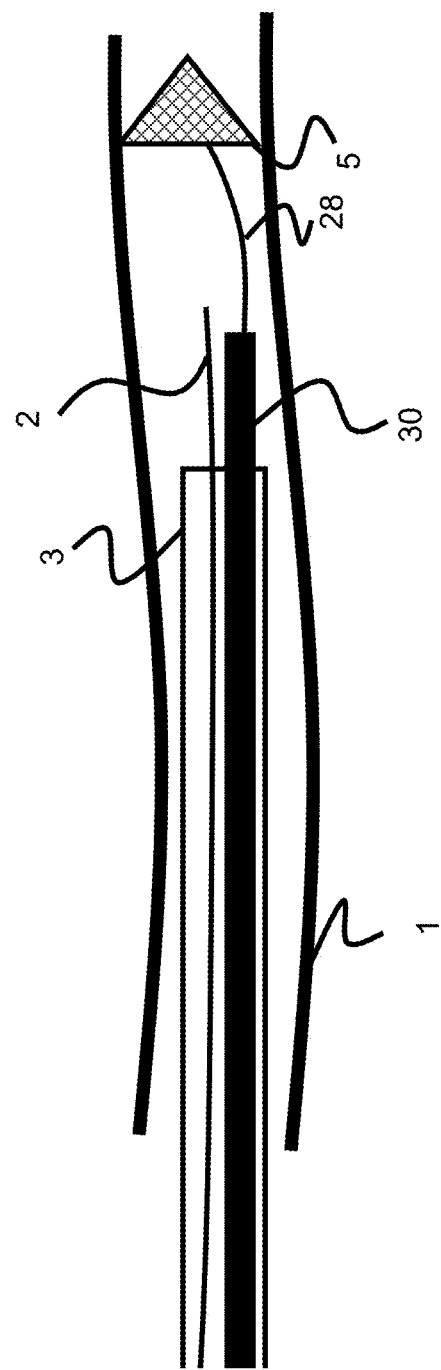
FIG. 1 illustrates an embodiment of a distal end of a guide wire, guide catheter, delivery sheath, implant delivery wire, and an implant, according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Delivery of implants or vascular devices such as EPDs, filters, coils, plugs, occluders, stents, clot retrievers, or other implants are typically delivered via relatively small catheters or delivery devices since the medical procedures often take place in smaller blood vessels, such as those in the head. Despite this small size, the delivery system must both have a high push strength to get the device to the treatment site and must be able to navigate a potentially tortuous vasculature.

Traditional delivery methods typically involve using a guide catheter 3 to get near a treatment area of a vessel 1, as seen in FIG. 1. A guidewire 2 is first advanced through the patient's vessel 1 until its distal end is positioned at or near the treatment area. Next, the guide catheter 3 is advanced over the guidewire 2 until its distal end is also located at or near the treatment area of the vessel 1. The implant 5 is then conveyed in a delivery sheath 30, catheter, or other delivery device through the guide catheter 3, until the distal end of the sheath 30 is located at the treatment site. Finally, the implant 5 can be pushed out of the sheath 30 by advancing the attached delivery wire 28 or the sheath 30 can be retracted to expose the implant 5.

Due to the turbidity associated with blood flow, the potentially limited space available at the treatment site due to smaller blood vessel size (among other factors), and the tendency of the implant 5 to move as the sheath 30 is retracted, the delivery process remains difficult. If the implant 5 displaces considerably during delivery, the surgeon must again navigate the implant 5 to the treatment site, which may require precious time during an invasive procedure.

In this regard, embodiments of the present invention are directed to a delivery system that allows a physician to both lock the position of the implant 5 and its delivery wire 28 relative to the target site within the patient, while also retracting and removing the outer delivery sheath 30 via a proximal cutting device (either partial or full removal). Hence, the outer delivery sheath 30 can be quickly withdrawn and separated from the delivery wire 28 during a procedure without the need to unlock the delivery wire 28 from proximal portions of the delivery system.

The following embodiments utilize a sheath cutting system to cut the sheath 30 while the sheath is retracted to expose and deploy the implant 5. In one embodiment, the implant delivery system is used to deliver an embolic protection device (EPD) having an attached implant wire. Embolic protection devices are a type of blood vessel filter. They are often placed distal to a treatment site. In one example, a stent or balloon is used to expand a calcified area to enable blood flow in a region where thrombus has formed. Prior to delivering the stent or balloon, the embolic protection device or filter is placed downstream of this target area, and any thrombus dislodged by the stent or balloon is caught by the EPD or filter so that the thrombus does not collect at a distal location and cause later problems. The EPD or filter can be withdrawn at a later time. Though the terms implant wire or delivery wire are used, these terms may include wires, hypotubes, rods, or other mechanisms, and are further broadly intended to refers to an element which is connected to or on which the implant is mounted.

Figure 2:
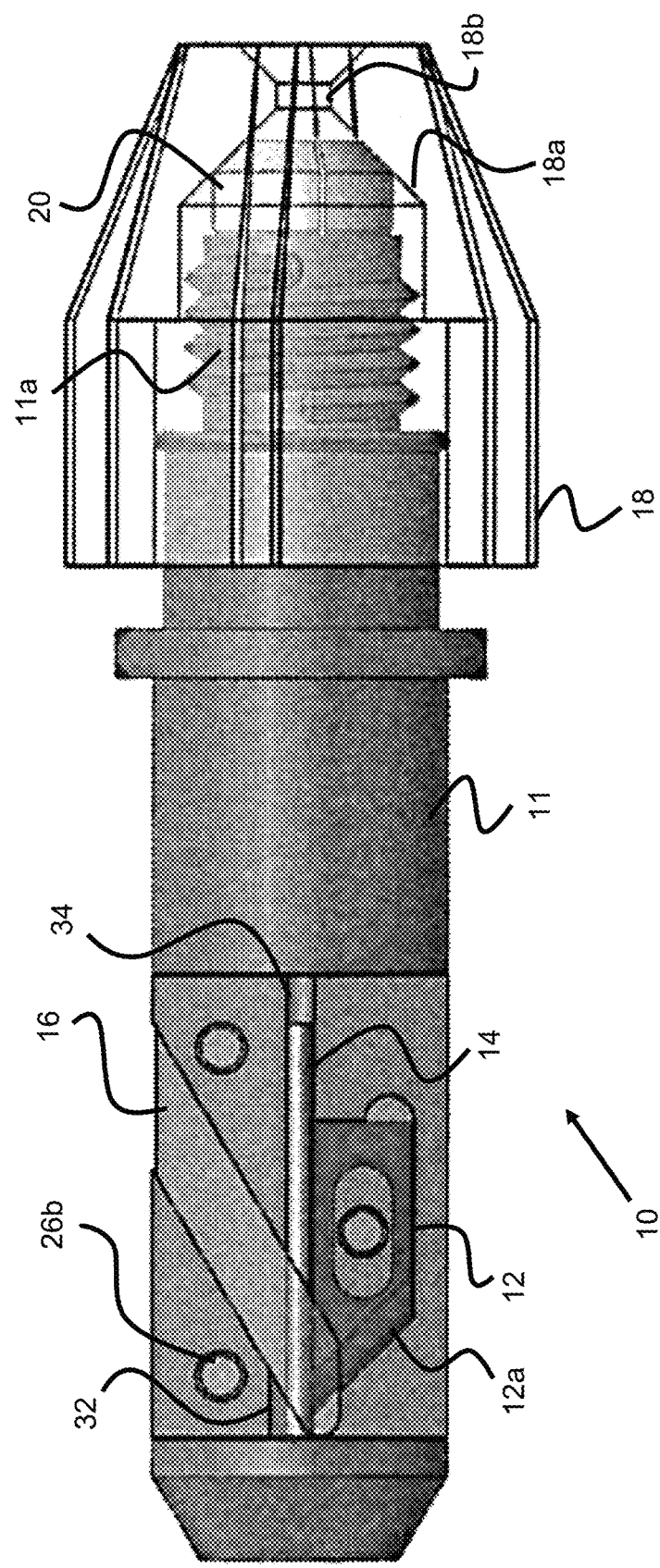
FIGS. 2-4 illustrate an embodiment of a torque device used in an implant delivery system according to the present invention.
Figure 3:
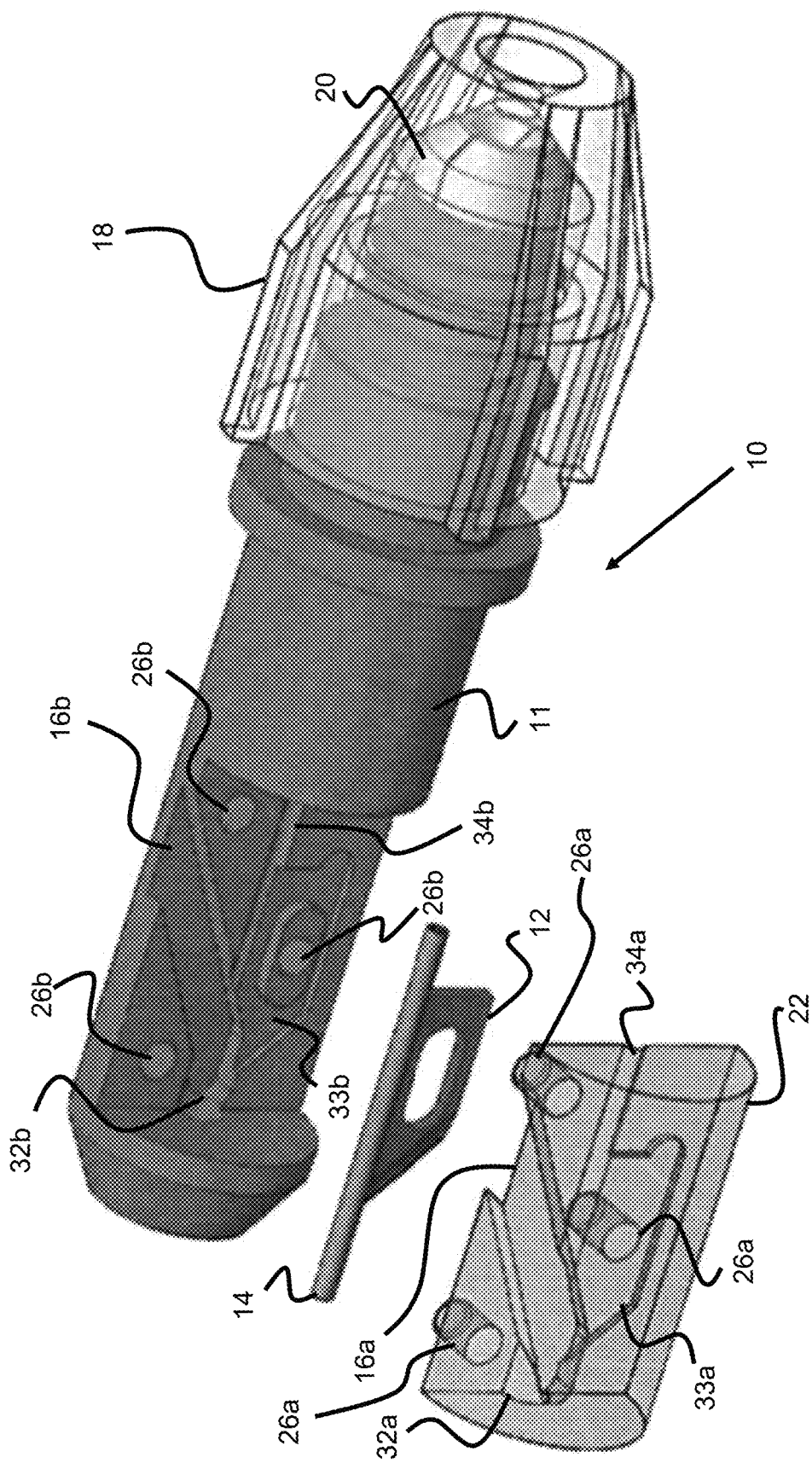
Figure 4:
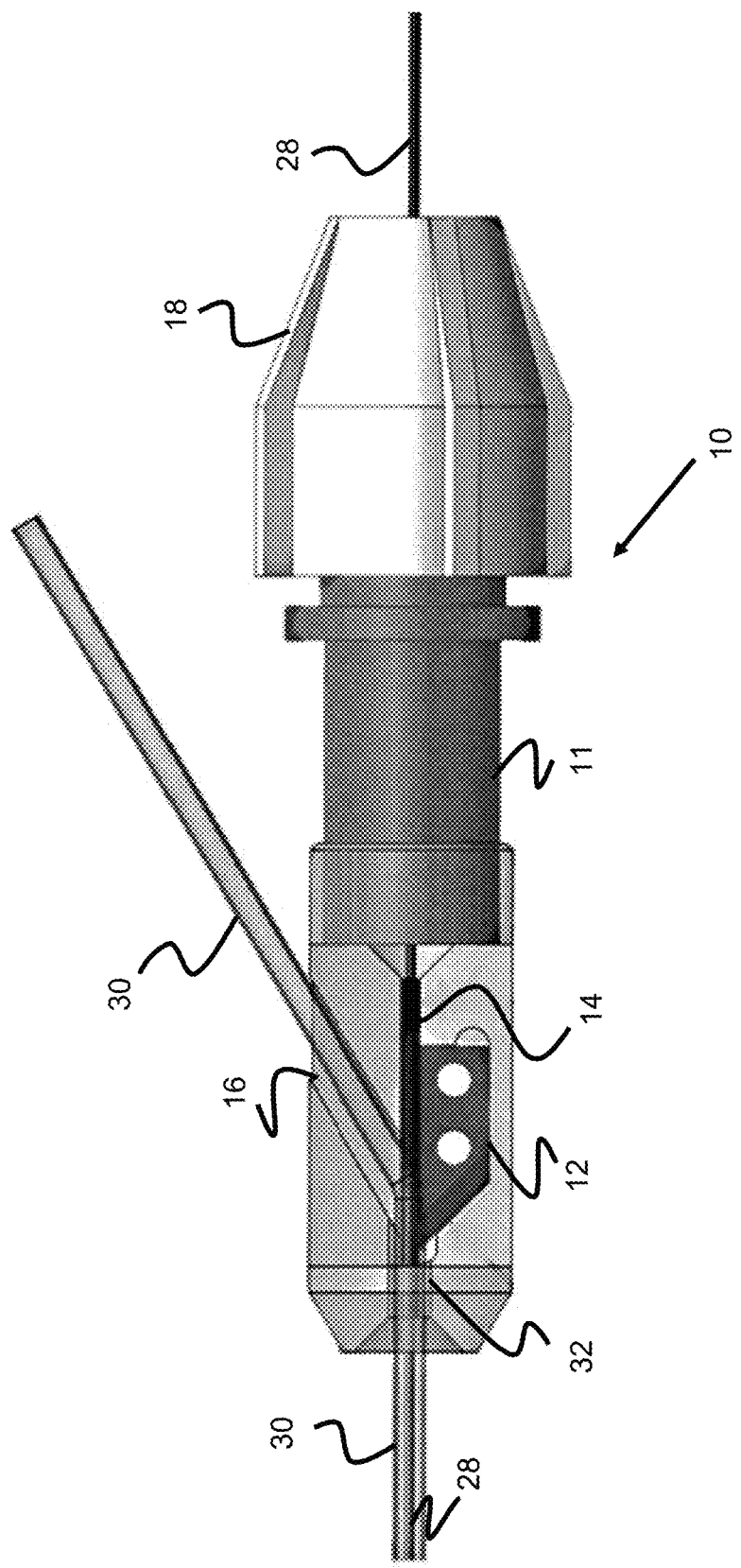

FIGS. 2-4 illustrate various aspects of a torque device 10 that is located at a proximal portion of the implant delivery system. The torque device 10 preferably is located proximal of the guide catheter 3 during a procedure, since the implant delivery system utilizes the guide catheter 3 to navigate the implant to the appropriate treatment site within the vasculature 1. With regard to the figures, the left side is distal and the right side is proximal relative to the procedure into the patient. Hence, the left side of the torque device 10 is located next to or near the proximal end of the guide catheter 3, the implant 5 is connected to the distal end of the implant wire 28 (see FIG. 1), and the implant is located either in the guide catheter 3 or in the blood vessel 1 if the implant is already delivered.

As previously discussed, the torque device 10 includes a cutting mechanism for slitting and separating the sheath 30 from the delivery wire 28, as well as a locking mechanism for locking the position of the delivery wire 28 relative to the torque device 10. Turning first to the cutting mechanism, its purpose is to cut the sheath 30 (see FIGS. 1 and 4) as the sheath 30 is retracted to expose the implant 5 at the treatment site. The torque device 10 includes a cutting element 12 that is preferably configured to only cut one face or side of the sheath, so as to create a slit running longitudinally through the length of the sheath 30. In one example, the cutting element 12 is a sharpened blade composed of metal or a hardened polymer.

The distal portion of a body member 11 of the torque device 10 includes a common passage 32 into which both the sheath 30 and the implant wire 28 traverses through. The common passage 32 separates into sheath lumen 16 and implant wire lumen 34 at a more proximal location (best seen in FIG. 2). However, the common passage and the implant wire lumen 34 are aligned with each other and can alternately be considered a single elongated passage. The cutting element 12 is located near this branched location so that a sharpened edge 12a is oriented in a distal direction and protrudes into the common passage 32 just enough to cut through the bottom of the sheath 30. The cutting element 12 includes a separator passage 14 that is generally aligned and located within the implant wire lumen 34 to allow passage of the implant wire 28. The sheath lumen 16 is angled away from the cutting element 12 and the implant wire lumen 34 (e.g., in a direction opposite of or away from the cutting element 12) so as to direct the slit sheath 30 in a direction askew or away from the implant wire 28. The implant wire 28 exits the sheath 30 through its cut slit and thereby is able to maintain its position in the torque device 10.

In one embodiment, the sheath 30 may include a weakened region or a pre-formed slit that is aligned with the sharpened edge 12a of the cutting element 12 to ease the cutting process. For example, this weakened or pre-formed slit may be located at the proximal end or edge of the sheath 30. In another embodiment, the sheath 30 does not have a weakened region or a pre-formed slit and the sharpened edge 12 is sufficient to slit the sheath.

The proximal end of the torque device 10 includes a clamping mechanism that selectively clamps the implant wire 28 in place. More specifically, a collet 20 is located at the proximal end of the torque device 10, having a passage through it that aligns with the implant wire lumen 34. The body 11 of the device 10 includes a threaded portion 11a located on a proximal end of the body 11, around and/or adjacent to the collet 20. A mating thread is located on an interior of a screw element 18, allowing the screw element 18 to screw onto the body, over the collet 20. A proximal passage 18b on the end of the screw element 18 allows the implant wire 28 to pass through as needed.

As the screw element 18 is screwed distally onto the thread 11a of the body 11, its internal surface 18a presses against outer angled surfaces of the collet 20, causing the collet 20 to compress or decrease the size of its internal passage. If the implant wire 28 is positioned though the collet 20, the collet 20 will compress or clamp around the wire 28, fixing it in longitudinal and rotational position relative to the torque device 10. Rotating the screw element 18 in the opposite direction so as to move it proximally relative to the body 11 causes the internal surfaces 18a of the screw element 18 to move away from the collet 20, releasing the compression or clamp on the implant wire 28 and allowing movement of the wire 28 relative to the body 11. Since the implant wire 28 can be fixed, the implant 5 is similarly fixed since it is connected to the implant wire 28 at its distal end. Thus, the physician can lock the collet 20 to lock the position of the implant 5 in the patient and retract the sheath 30 to expose the implant 5 so that the implant 5 will stay relatively fixed at the distal end of the device. While high turbidity due to blood flow may cause some minor implant movement, locking the collet 20 generally reduces any substantial movement that might otherwise occur.

The collet 20 can be selected from numerous different designs. For example, the collet 20 can be composed of spring steel, with one or more kerf cuts along its length to allow it to expand and contract as the screw element 18 moves away from or against it. Another example embodiment for the collet 20 is one that has several tapered metal blocks held in circular position (like the points of a star, or indeed the jaws of a jawed chuck) by a flexible binding medium (e.g., synthetic or natural rubber).

One disadvantage of traditional delivery systems is that the implant can move around upon delivery due to the mechanical interplay between the sheath and the implant when the implant is pushed or the sheath is retracted. Since the user in the present embodiments can lock the implant in place via the clamping mechanism (screw member and collet), the implant delivery proceeds more smoothly since the implant better maintains its position.

Figure 5:
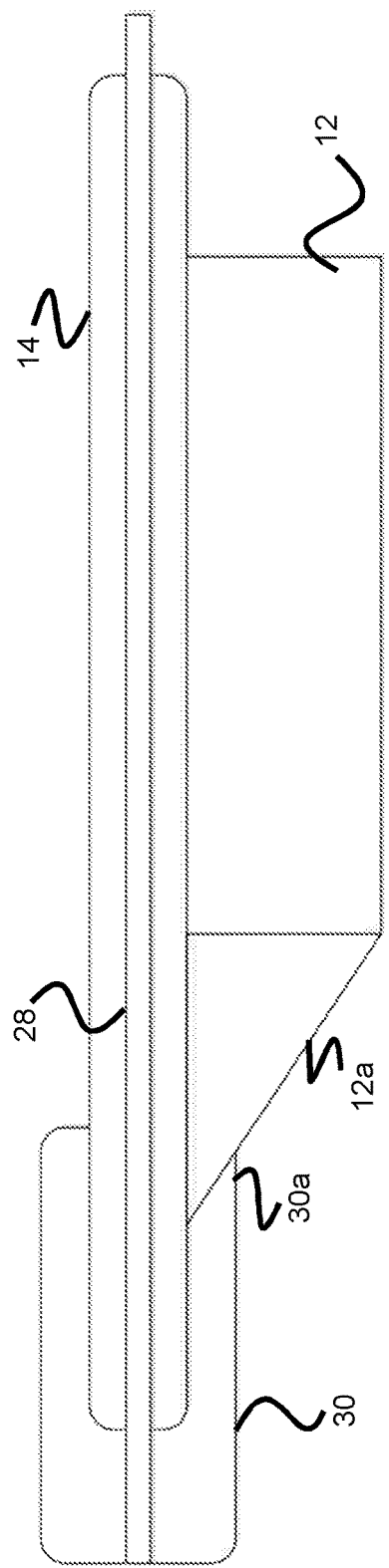
FIG. 5 illustrates an embodiment of a cutting element from a torque device used in an implant delivery system according to the present invention.

As previously noted, the torque device 10 includes a separator tube 14 to ensure the sheath and implant wire separate from each other, respectively, into passages 16 and 34. In one example, the separator tube 14 is a polymeric tube and is located just above the cutting element 12 in a portion of the common passage 32 and extending into the implant wire passage 34 (see FIGS. 3-5). The separator tube 14 can also be metallic in other examples. As best seen in FIG. 5, the sheath 30 is proximally pulled around the proximal end of the separator tube while the implant wire 28 passes through the interior of the separator tube 14 and into the implant wire lumen 34. The sharpened edge 12a of the cutting element 12 extends or is adjacent to the bottom of the separator tube 14, thereby allowing the cutting element 12 to cut the bottom portion 30a of the sheath 30 as the sheath 30 passes past the cutting element 12.

In one embodiment, the body member 11 entirely forms the passages 16, 32, and 34 of the torque device 10. In another embodiment, several discrete components make up the torque device 10, as shown in FIGS. 2 and 4. The passage 16, 32, and 34 in FIG. 2 are better shown in the exploded view of FIG. 3 in which a mating piece 22 connects to and mates with the body member 11 to define the passageways integral to the torque device 10.

Specifically, passages 16, 32, and 34 are composed of recessed portions 16a, 32a, and 34a on the mating piece 22, and recessed portions 16b, 32b, and 34b on the body member 11. Once connected, the recesses line up with each other to create the afore-mentioned passages 16, 32, and 34. Preferably, the recessed portions have a depth that is equal on both the body member 11 and the mating piece 22, such that each recess makes up about half of structure of the passages 12, 32, and 34. Alternately, the recesses may make up unequal portions of the passages or only one of the components (e.g., the body member 11) may have recesses, while the other component (e.g., the mating piece) may have a flat, non-recessed portion that presses against and completes the passages 16, 32, and 34 (i.e., the diameter of these passage may not be completely circular).

As best seen in FIG. 3, the mating piece 22 and the body member 11 have apertures 26a and 26b, respectively, that can be aligned with each other. Once aligned, a screw or another mechanical attachment mechanism can be placed through both holes 26a and 26b to bind the mating piece 22 to the body member 11. Alternately, the mating piece 22 may include posts instead of apertures, that enter into the apertures 26b of the body 11 and can be used with adhesive or other known binding materials and techniques.

One advantage of manufacturing the torque device 10 from multiple mated elements is that a separate, discrete cutting element 12 can be positioned or mounted between these elements. As shown in FIG. 3, the cutting element 12 (and optionally the separator tube 14) can be placed within the cavity formed by depressions 33a and 33b within the mating piece 22 and body member 11 of the torque device 10.

Figure 6:
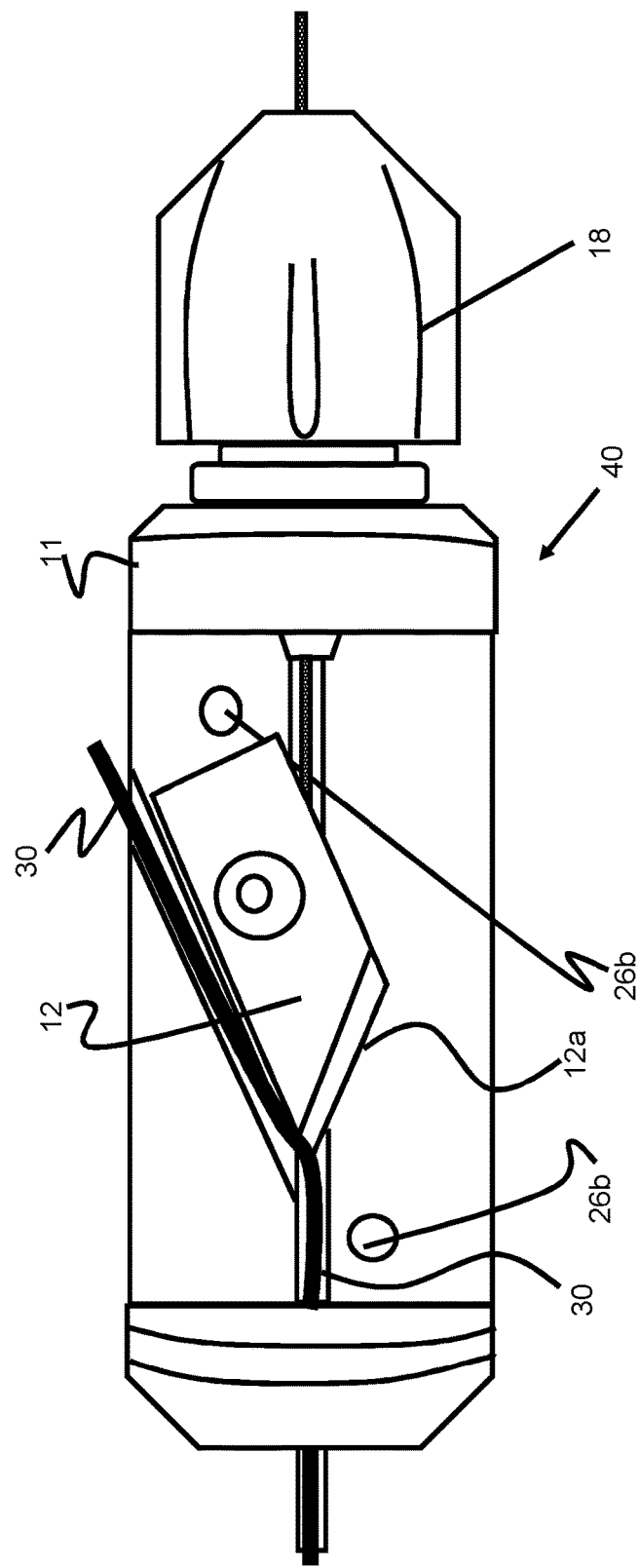
FIG. 6 illustrates an alternate embodiment of a torque device used in an implant delivery system according to the present invention.

FIG. 6 illustrates another embodiment of a torque device 40 that is generally similar to the previously described torque device 10. However, while the torque device 10 of FIGS. 2-4 positions the cutting element 12 near the bottom of the passageway 32, before the common passage 32 splits into sheath passage 16 and implant wire passage 34, the torque device 40 of FIG. 6 positions a cutting element 12 mounted integral with sheath passage 16, near the front/distal portion of sheath passage 16. The sharpened edge 12a of the cutting element 12 is positioned distally at a similar angle as that shown for the torque device 10 to cut or split a portion of the sheath 30 as it passes by. Since the cutting element 12 is located within the sheath passage 16, a separator tube 14 is unnecessary since the common passage 32 has already branched into sheath passage 16 and implant wire passage 34.

In operation, the torque device 10 is placed proximal to a guide catheter 3, outside of the patient's body. The guide catheter is navigated through the patient vasculature over a guidewire 2 to an appropriate location in the vicinity of the target treatment site. The guidewire 2 is then withdrawn so the lumen of the guide catheter 3 can be used to deliver the delivery sheath 30 (note that FIG. 1 illustrates both the sheath 30 and guide wire 2 in the guide catheter 3 simultaneously for ease of illustration only). The delivery sheath 30 is tracked through the guide catheter 3 and placed at or near the treatment site. The implant 5 is either pre-loaded near the distal end of a delivery sheath 30 or is tracked through the delivery sheath 30.

The implant 5 is mounted on, or connected to, implant delivery wire 28. Once the delivery sheath 30 is placed, the delivery sheath 30 is withdrawn through the torque device 10. The delivery sheath 30 passes proximally through the common passage 32, is slit by cutting element 12, and moves axially askew away from the implant delivery wire 28 through sheath passage 16. Prior to withdrawing the delivery sheath, the implant delivery wire 28 can optionally be fixed by rotating the screw element 18 so the collet 20 compresses against the implant delivery wire 28, maintaining the implant 5 in a relatively fixed position in the patient as the delivery sheath 30 is withdrawn.

After deployment, the implant delivery wire 28 can act as a guidewire for tracking additional devices. In one example where the implant 5 is an EPD or filter, the implant 5 is placed distal to a target treatment site. Once the EPD/filter is placed and the sheath 30 is withdrawn and slit, the implant delivery wire 28 is used as a guidewire to track a stent or balloon to a treatment site to treat a calcified area. The stent or balloon may utilize the still-placed guide catheter 3 as a conduit, or another delivery catheter can be tracked over the implant delivery wire 28. The stent or balloon is placed proximal of the EPD/filter. The stent or balloon is expanded to prop open a blood vessel 1, and any dislodged thrombus is caught by the EPD/filter, which sits in a distal location. After the operation, at a later time, the EPD or filter can be withdrawn by utilizing a retrieval catheter and pinning the EPD/filter against the retrieval catheter to withdraw the device.

Other embodiments utilize a rapid exchange guidewire system. In one example, the guide catheter 3 has a side port to accommodate exit and entry of the guidewire 2. Thus the guidewire 2 does not need to be tracked through the entire length of the guide catheter 3. The guidewire 2 is placed through the side port of the guide catheter 3 and the guide catheter 3 is pushed over the guidewire 2. Once the guide catheter 3 is placed, the guidewire 2 is withdrawn via the side port, and the delivery sheath 30 (and implant 5 housed therein) is pushed through the guide catheter 3 to the treatment site.

Other devices utilize a rapid exchange guidewire system in which the implant 5 itself contains a port to accommodate the guidewire 2. The guidewire 2 can be pre-loaded through the implant 5, where the implant 5 is located within a delivery sheath 30 and the delivery sheath 30 is positioned within a guide catheter 3. The implant 5 and delivery sheath 30 can be pushed over the guidewire 2 to a treatment site. Once located at the treatment site, the guidewire 2 is withdrawn by pulling back on the guidewire 2. The guidewire 2 will retract through the implant 5 and either through the length of the guide catheter 3 or through a side-port of the guide catheter 3. The implant delivery wire 28 is then used as a conduit for additional implants, as detailed above.

The implant delivery system can be used to deliver a multitude of implants such as EPDs, filters, coils, plugs, occluders, stents, clot retrievers, or other implants. The method of use embodiments described above detailed how one may use the implant wire of an EPD as a mechanism to deliver further implants, but this same principle can be applied where implants other than EPD's are used.

Delivering an implant 5 via a delivery sheath 30 and retracting the delivery sheath 30 through a torque device 10 mechanism to cut the sheath 30 and expose the implant 5 can also be used for a multitude of implants. The ability to fix the implant position via compressing the collet 20 on the torque device 10, and the ability to expose the implant 5 by cutting the delivery sheath 30 are features of this technique.

Variations of the methods and embodiments of this invention further include using the screw 18 and collet 20 configuration to lock the implant wire 28, and subsequently retracting the delivery sheath 30, but without using a cutting element 12. In such an embodiment, the implant 5 is in a fixed position and the delivery sheath 30 would simply be retracted through the torque device 10 instead of cut. Thus, a device similar to the torque device 10 of FIGS. 1-5 may be used, except without the cutting element 12. The delivery sheath 30 is instead retracted through sheath passage 16 without being cut. This embodiment may be used on a multitude of implants such as coils, stents, EPD's, filters, plugs, occluders, clot retrievers, or other implants. One or more of these devices are fixed or connected to an implant delivery wire 28 and delivered through a delivery sheath 30. The delivery sheath 30 may then be withdrawn to expose the implant. The user may optionally lock down the implant via compressing the collet 20 over the delivery wire 28 to minimize movement of the implant during the delivery operation.

Any measurements, figures, materials described herein are only meant to be illustrative in nature and not meant to be specifically limited to what is literally disclosed.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An implant delivery system comprising:
an implant configured for providing medical treatment inside a human body and being operatively connected to an elongated implant wire;
a sheath having a lumen, the implant and the elongated implant wire being sized for deployment through the sheath;
a torque device comprising:
    a torque body having an indented section and a non-indented section;
    a mating piece that removably connects to and mates with the torque body;
    a first passage extending through the torque device, the first passage comprising recessed areas in the indented section of the torque body and recessed areas in the mating piece that align with each other, the first passage continuing through the non-indented section of the torque body;
    a separator passage member removably located within the first passage and allowing passage of the elongated implant wire; the separator passage member comprising a tube and a cutting element that is fixed to the tube and positioned proximally of a distal end of the tube; the separator passage member having a distal end located at a location proximal of the first passage distal opening;
    a second passage connecting to the first passage near the cutting element, the second passage extending away from the first passage, the second passage comprising recessed areas in the indented section of the torque body and recessed areas in the mating piece that mate with each other;
    a clamp mechanism which selectively presses against the elongated implant wire;
    the cutting element is positioned in the first passage in between the torque body and the mating piece to slit a sheath passing through the first passage, wherein the torque device directs the slit sheath into the second passage while leaving the implant in place.

2. The implant delivery system of claim 1 wherein the torque device has a proximal end and a distal end, and a longitudinal axis extending therebetween; and wherein an external opening of the second passage is perpendicular to the longitudinal axis of the torque body.

3. The implant delivery system of claim 2, wherein the separator passage member has a distal end located proximally of a distal end of the first passage.

4. The implant delivery system of claim 2 wherein the body member and the mating piece both include recesses which form the second passage.

5. The implant delivery system of claim 2 wherein the body member and the mating piece both have apertures which align to facilitating connection between the body member and the mating piece.

6. The implant delivery system of claim 1 wherein the medical implant is an embolic protection device.

7. A method of delivering an implant comprising:
locking a clamp mechanism on a torque device to an elongated implant wire; a distal end of the implant wire being operatively connected to an implant configured for providing medical treatment inside a human body;
proximally withdrawing a sheath through the torque device; the sheath being at least partially disposed over the elongated implant wire; the sheath first passing through a distal opening of the torque device and into a first passage, and then passing over an outside of a separator passage member; the separator passage member being removably located in the torque device, and comprising a tube and a cutting element that is connected to the tube and positioned proximally of a distal end of the tube;
creating a longitudinal slit portion in the sheath with the torque device; and,
separating the longitudinal slit portion of the sheath from the elongated implant wire, wherein the sheath is directed from said first passage to a second passage that is directed away from the elongated implant wire; the second passage having an external opening aligned along a side of the torque device;
wherein the torque device comprises a torque body with a proximal portion and a distal portion that has a cut-away shape relative to the proximal portion and wherein a mating piece mates with the distal portion to form the first passage and the second passage; and wherein the first passage is further formed from a unitary region in the proximal portion of the torque body.

8. The method of claim 7, wherein the locking a clamp mechanism further comprises screwing a screw member of the clamp mechanism on to a collet of the clamp mechanism.

9. The method of claim 7, wherein the creating a longitudinal slit portion further comprises passing the sheath over a cutting element in the torque device.

10. The method of claim 7, wherein the proximally withdrawing the sheath further comprises expanding the implant within a patient.

* * * * *